United States Patent
Luryi et al.

(10) Patent No.: US 6,944,407 B2
(45) Date of Patent: Sep. 13, 2005

(54) METHOD AND APPARATUS FOR DETECTING RADIATION

(75) Inventors: Serge Luryi, Old Field, NY (US); Vera Gorfinkel, Stony Brook, NY (US); Mikhail Gouzman, Lake Grove, NY (US)

(73) Assignee: The Research Foundation of State University of New York, Stony Brook, NY (US)

( * ) Notice: Subject to any disclaimer, the term of this patent is extended or adjusted under 35 U.S.C. 154(b) by 0 days.

(21) Appl. No.: 10/322,293

(22) Filed: Dec. 18, 2002

(65) Prior Publication Data

US 2003/0123883 A1 Jul. 3, 2003

Related U.S. Application Data

(62) Division of application No. 09/186,248, filed on Nov. 4, 1998, now Pat. No. 6,528,801.

(51) Int. Cl.[7] .................. H04B 10/06; H04B 10/158
(52) U.S. Cl. .................. 398/202; 398/151; 398/186; 380/229; 380/256; 380/263
(58) Field of Search ................... 398/186, 98, 101, 398/102, 103, 151, 156, 202, 203; 380/263, 203, 210, 229, 256

(56) References Cited

U.S. PATENT DOCUMENTS

| | | | |
|---|---|---|---|
| 5,171,534 A | | 12/1992 | Smith et al. |
| 5,757,912 A | * | 5/1998 | Blow .................. 380/256 |
| 5,784,157 A | | 7/1998 | Gorfinkel et al. |
| 5,793,049 A | | 8/1998 | Ballard |
| 5,818,057 A | | 10/1998 | Buck |
| 5,940,545 A | | 8/1999 | Kash et al. |
| 6,043,506 A | | 3/2000 | Heffelfinger et al. |
| 6,071,748 A | | 6/2000 | Modlin et al. |
| 6,137,584 A | | 10/2000 | Seidel et al. |

FOREIGN PATENT DOCUMENTS

WO  9823941  4/1998

OTHER PUBLICATIONS

"Coded multipulse modulation in optical communication systems"; Atkin et al; Communications, IEEE Transactions on, vol.: 42, Issue: 234, Feb.–Apr. 1994, pp.: 574–582.*
D.Y. Chen et al., "Single Molecule Detection in Capillary Electrophoresis: Molecular Shot Noise as a Fundamental Limit to Chemical Analysis," Analytical Chemistry vol. 68, pp. 690–696 (1996).
W.R. McCluney, "Introduction to Radiometry and Photometry," Artech House, Jun. 30, 1994, pp. 114–122.
Alan Smith, "Selected Papers on Photon Counting Detectors," SPIE (Milestone Series), vol. MS413, Feb. 4, 1998 (ISBN: 0–8194–2788–8), pp. 194–202, published by the Society of Photo–optical Instrumentation Engineers (SPIE).

* cited by examiner

*Primary Examiner*—M. R. Sedighian
*Assistant Examiner*—Nathan Curs
(74) *Attorney, Agent, or Firm*—Baker Botts LLP

(57) ABSTRACT

In analyzing radiation from a communication link, single-photon counting can be used to advantage especially at low levels of radiation energy, e.g. in the detection of optical radiation. Preferred detection techniques include methods in which (i) received optical radiation is intensity-modulated in accordance with a preselected code, (ii) wherein it is the optical radiation which is intensity-modulated with the pre-selected code, and (iii) wherein the radiation modulated with a preselected code is received. For registration of the signals received by a sensing element of a single-photon detector, time of arrival is recorded, optionally in conjunction with registration of time intervals. Advantageously, in the interest of minimizing the number of pulses missed due to close temporal spacing of pulses, D-triggers can be included in counting circuitry.

3 Claims, 2 Drawing Sheets

METHOD AND APPARATUS FOR DETECTING RADIATION

TECHNICAL FIELD

The invention is concerned with analytical technology and, more specifically, with the detection of a fluorescent species or fluorophore in a sample. This application is a division of application Ser. No. 09/186,248, filed 4 Nov. 1998, now U.S. Pat. No. 6,528,801.

BACKGROUND OF THE INVENTION

Fluorescent species or fluorophores emit fluorescent radiation when suitably stimulated by stimulating radiation. The emitted radiation can be used for chemical/biological analytic purposes, e.g. in determining whether a fluorophore of interest is present in a sample and in quantifying its concentration. One analytic technique of this type is disclosed in U.S. Pat. No. 5,171,534 to Smith et al. wherein DNA fragments produced in DNA sequencing are characterized on the basis of fluorescence of chromophores tagged to the fragments. Stimulating electromagnetic radiation may be monochromatic, or may include significant energy in a plurality of energy bands, e.g. as disclosed in U.S. Pat. No. 5,784,157 to Gorfinkel et al.

The stimulating radiation usually varies in time, either stochastically or regularly. Regular variation of the radiation intensity can be introduced artificially by modulating the intensity of the radiation source or the transmittance or reflectance of a filter element in the optical path. Regularly modulated radiation may be termed as encoded radiation if the temporal variation of the radiation is used as a carrier of information. Associated with such encoded radiation is a temporal code, i.e. a time-domain function which corresponds to the temporal evolution of the intensity of modulated radiation. A time-domain function can be formed as a linear combination of several suitable functions whose respective contributions to the linear combination can be quantified reliably. Suitable in this respect are sinusoidal functions of time, for example, oscillating at distinct frequencies.

In prior-art techniques, the encoded radiation is considered as continuous, with the time dependence of detected radiation intensity regarded as a continuous time-domain function.

Further background includes several known single-photon detection techniques for which W. R. McCluney, *Introduction to Radiometry and Photometry*, Artech House, 1996, pp. 114–122 provides a general introduction. Such techniques are designed for measuring modulated radiation, and they can be classified into two groups: (a) asynchronous photon counting and (b) synchronous detection. As described in Alan Smith, *Selected Papers on Photon Counting Detectors*, SPIE, Vol. MS 413, 1998, methods (a) of asynchronous photon counting involve the detection of a number of photons during a fixed time interval, e.g. one second, called the registration interval. These methods allow the determination of an average frequency of photon arrival. This frequency varies in time, either stochastically or regularly, and synchronous counting can be employed to measure the time variation. An essential limitation of this method is associated with the impossibility of measuring frequencies of modulation that are higher than the repetition rate of registration intervals. This difficulty is inherent in the principle of asynchronous counting, which is to keep track of the total number of photons received during the registration interval rather than register their times of arrival. A difficulty arises when the highest frequency $f_{mod}$ in the modulation spectrum of modulation radiation is comparable to or higher than the average frequency $f_{phot}$ of single-photon detection. In this case, if the frequency limit is increased by reducing the time interval chosen for counting, the technique becomes increasingly inefficient because the counter will count nothing during most registration intervals.

Methods (b) of synchronous detection involve measurement of the time of arrival of incident single photons. This time may be referenced to an "absolute" clock, or may be measured relative to or "synchronously with" a triggering excitation signal. The triggering signal may be associated with the arrival of the first of detected photons, for example. Such methods are particularly valuable for application to fast processes, e.g. the fluorescent decay of a single excited dye molecule as described, e.g., by D. Y. Chen et al., "Single Molecule Detection in Capillary Electrophoresis: Molecular Shot Noise as a Fundamental Limit to Chemical Analysis", *Analytical Chemistry*, Vol. 68 (1996), pp. 690–696, typically requiring special electronics for handling fast temporal variations. An essential limitation of these methods is associated with the difficulty of maintaining records of high temporal resolution for a relatively long time. Thus, detecting photon arrivals at the temporal resolution corresponding to nanosecond time intervals over a one-second period requires acquisition of a billion data records. This makes methods of synchronous detection difficult to apply to the photometry of relatively slowly varying modulated single-photon fluxes.

SUMMARY OF THE INVENTION

We have recognized that, in detecting a fluorescent species in a sample, single-photon counting can be used to advantage, especially at low levels of fluorescent signal energy. Preferred detection techniques include methods in which (i) fluorescence-stimulating radiation is intensity-modulated in accordance with a preselected code, (ii) wherein it is the fluorescent radiation which is intensity-modulated with the preselected code, and (iii) wherein modulation with a preselected code is applied to a sample to influence a property, e.g. temperature, pressure, or an electric or magnetic field strength or frequency which functionally affects emitted fluorescent radiation.

Preferably, for registration of the signals from a sensing element of a single-photon detector, time of arrival is recorded, optionally in conjunction with registration of time intervals. Advantageously, in the interest of minimizing the number of pulses missed due to close temporal spacing of pulses, D-triggers can be included in counting circuitry.

The preferred techniques are generally applicable to photometry of time-encoded single-photon or particle fluxes. They involve measurement of time intervals between single-photon/particle arrivals combined with data analysis that permits decoding of the encoded radiation, i.e., discrimination between alternative possible codes and quantification of different combinations of mixtures of the codes. The techniques provide for the time intervals between successive pulses to be measured asynchronously, without requiring an external clock reference or special triggering signal. They provide for efficient measurement and decoding of time-encoded single-photon or particle fluxes.

DETAILED DESCRIPTION

For purposes of the present description, no distinction need be made between "photon" and "quantum", as each can result in a detector signal, typically an electrical signal or pulse for electronic processing in accordance with techniques of the invention. Use of other types of signal processing is not precluded, e.g. by opto-electronic or purely optical means. It is understood that, in alternative processing means, a detector signal or a pulse being processed can be other than an electric signal or pulse.

A. Single-Photon Detection in Methods for Fluorophore Identification

A special illumination technique is used, with a plurality of modulated narrow-band sources, each modulated according to its own distinguishable time-domain function. The narrow-band sources excite different fluorophores differently, so that the emitted fluorescent radiation is encoded with information about the nature and composition of illuminated fluorescent species. Photons are detected individually.

Figure 1:
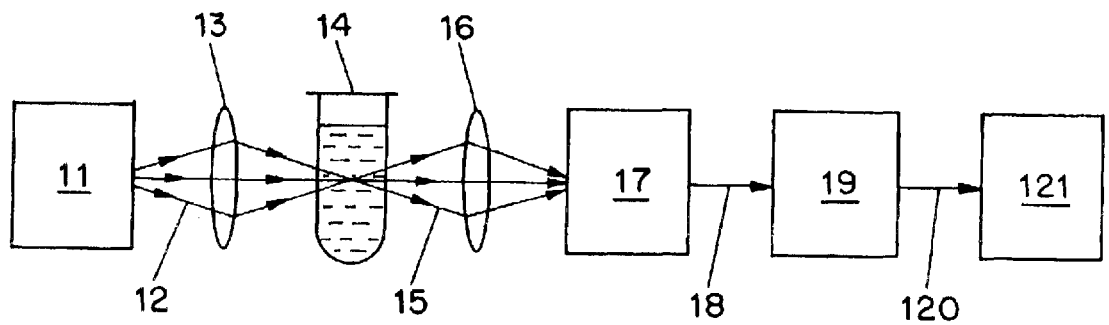
FIG. 1 is a schematic of a preferred first technique in accordance with the invention, using a modulated light source.

In a preferred first embodiment as illustrated by FIG. 1, a modulated multi-band light source producing encoded radiation of excitation of fluorescence is combined with single-photon detection of encoded fluorescence signal.

FIG. 1 shows the light source 11 producing a radiation flux 12 which, via an optical illumination system 13, is incident on the container 14 holding a fluorescent sample. The radiation flux 12 comprises a plurality of spectral bands, each modulated according to its own distinguishable time-domain function. Fluorescent radiation 15 emitted by the fluorescent sample is received by an optical receiver system, e.g. an objective 16, and is directed to the optical input of a single-photon detector 17. The output of the detector 17 is a stochastic stream 18 of electric pulses of similar shape, and information about the intensity of the received fluorescent radiation in a set time interval is contained in the average frequency of the pulses arriving in the interval. The temporal characteristics of the stream 18 of electric pulses are registered in a suitable form by the recorder 19 which is described below in further detail, in connection with FIGS. 4 and 5. In a preferred embodiment, the stochastic stream of pulses is characterized in terms of the spacing in time between arrivals of successive pulses. The detection system may be complemented by communication means 120 for transferring the recorded information at an appropriate rate from the recorder 19 to a signal processor unit 121.

Figure 2:
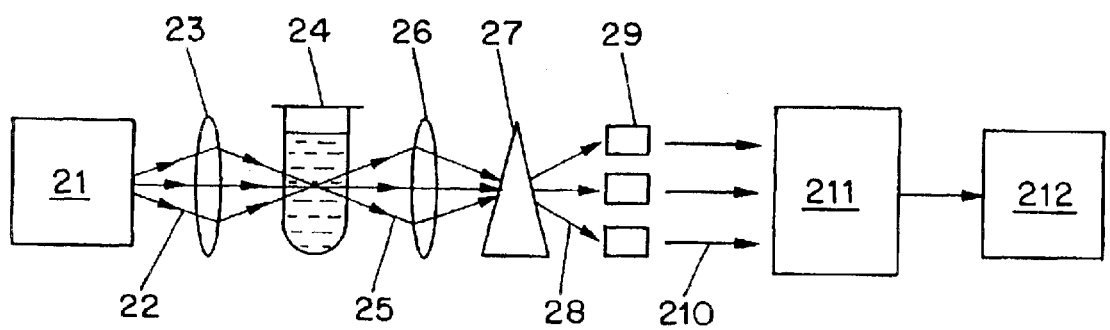
FIG. 2 is a schematic of a preferred second technique in accordance with the invention, using a dispersive element.

A preferred second embodiment as illustrated by FIG. 2 can be viewed as an improvement over a known method for multicolor fluorescent detection, e.g. as disclosed in the above-referenced patent to Smith et al. In this technique, the fluorescent radiation emitted by an excited molecule is optically analyzed into distinct wavelength channels, e.g. by a prism or a diffraction grating. The intensity of fluorescent radiation in each of the wavelength channels is then determined by photometric means. In the preferred second embodiment, sensitivity is enhanced by the use of single-photon detection.

FIG. 2 shows radiation 22 from a modulated optical source 21 being focused by a lens 23 onto a fluorescent sample 24. The modulated optical source 21 may produce one or several spectral bands that are modulated either together or independently with distinct time domain functions. Fluorescence 25 emitted by the sample 24 in response to the incident radiation 22 is directed by an objective 26 to an optical processor which comprises a dispersive element 27, e.g. a prism or a diffraction grating, and a set 29 of single photon detectors (SPD). The dispersive element 27 effects spectral analysis of the fluorescent signal.

Each of the SPD's produces at its output a stochastic stream of electrical pulses of similar shape, and information about the intensity of the received fluorescent radiation is contained in the temporal characteristics of the stochastic stream. With reference to FIG. 2, the temporal characteristics 210 from each SPD are registered by a recorder 211 whose structure is described below in further detail in connection with FIGS. 4 and 5. In a preferred embodiment, also described below in further detail in connection with FIGS. 4 and 5, the description of the stochastic stream of pulses is specified in terms of the time separations between arrivals of successive pulses. The detection system further comprises a signal processor unit 212 and means for transferring the recorded information at an appropriate rate from the recorder 211 to the signal processor unit 212.

FIG. 2 illustrates combination of a modulated light source for excitation of fluorescence with a dispersive element for analyzing the fluorescent response into distinct spectral bands, and single-photon detection of modulated fluorescence in each of the spectral bands. Additionally, as in FIG. 1, the modulated light source can be multi-band also, so that the radiation flux 22 comprises a plurality of spectral bands, each modulated according to its own distinct time domain function. In this case, a preferred technique is advantageous further in that different fluorescent species are distinguished both by their fluorescence emission spectrum and their fluorescence excitation spectrum. This enhances the fidelity of fluorophore identification.

Figure 3:
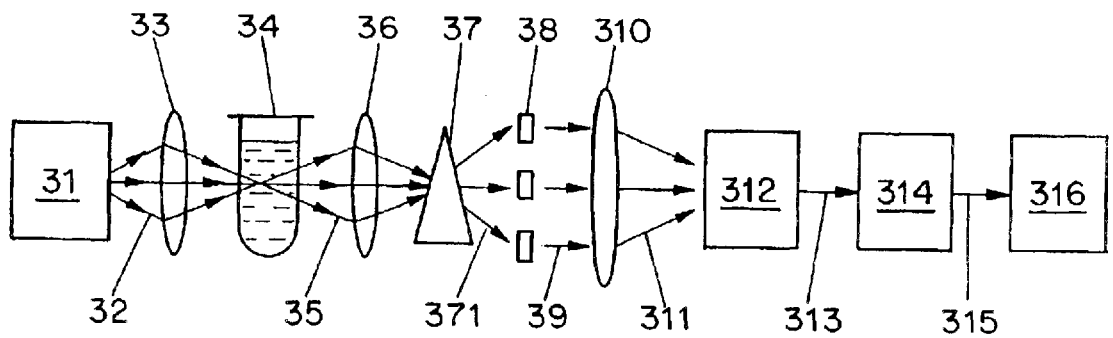
FIG. 3 is a schematic of a preferred third technique in accordance with the invention, involving temporal encoding of different spectral components of a fluorescent signal.

A preferred third embodiment of the invention, illustrated by FIG. 3, can be viewed as an improvement over a known technique for multicolor fluorescent detection, e.g. as applied according to the above-referenced patent to Smith et al. The known technique is combined with single-photon detection, using a modulation technique disclosed in U.S. patent application Ser. No. 08/946,414, filed Oct. 7, 1997 now abandoned, by Gorfinkel et al. In accordance with the latter technique, radiation reflected, transmitted, or fluorescently emitted by an object is encoded in such a way that the encoded radiation carries information about properties of the object, e.g. its color as characterized by reflected wavelengths, or the identity and quantitative content of fluorescent species present in the object. In the present embodiment of the invention, temporal encoding of different spectral components of a fluorescent signal is combined with single-photon detection of the encoded spectral components, for enhanced sensitivity.

FIG. 3 shows radiation 32 from optical source 31 being focused by an objective 33 onto a fluorescent sample 34. In contrast to the embodiments illustrated by FIGS. 1 and 2, the optical source 31 need not be modulated, and the radiation 32 may or may not be encoded. Fluorescence 35 emitted by the sample 34 in response to incident radiation 32 is directed by an objective 36 onto an optical processor which comprises a dispersive element 37, e.g. a prism or a diffraction grating, and a set of optical modulators 38. The dispersive element 37 effects spectral analysis of the fluorescence 35. The spectral components are directed onto a set of optical modulators 38 which modulate in time the resolved spectral components in such a way that each different resolved spectral component is coded by a distinct function of time. The modulated components 39 of the fluorescent spectrum are combined by an optical element 310 into an optical flux 311 focused onto the optical input of the single-photon detector 312. The output of the detector 312 represents a stochastic stream 313 of electrical pulses of similar shape, whose temporal characteristics are registered by the recorder 314 which is described below in further in connection with FIGS. 4 and 5. In a preferred embodiment, also described below in further detail, the description of the stochastic stream of pulses is specified in terms of the temporal separation between arrivals of successive pulses. The detection system further comprises means 315 for transferring the recorded information at an appropriate rate to a signal processor unit 316.

B. Single Photon Detection of Modulated Photon Fluxes

Figure 4:
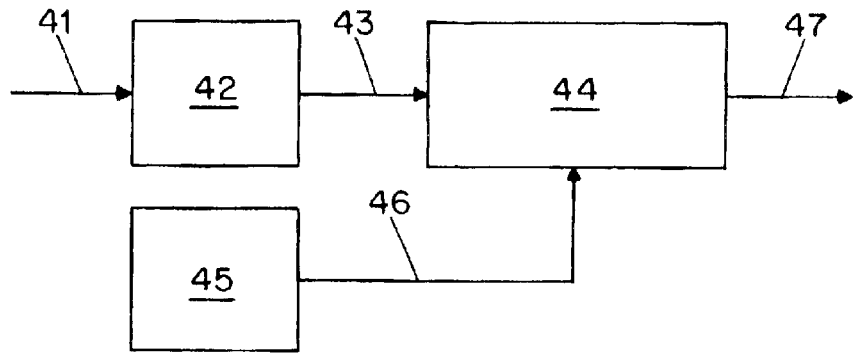
FIG. 4 is a schematic of a preferred fourth technique in accordance with the invention, for registration of temporal parameters of a stochastic sequence of pulses of constant or similar shape.

A preferred fourth embodiment of the invention is illustrated by FIG. 4, of a method for registration of temporal parameters of a stochastic sequence of pulses of constant or similar shape.

The recorder of FIG. 4 operates with a controlled time resolution, controlled by a clock 45 which provides a regular sequence 46 of electrical pulses of constant shape which define the recording time intervals. A stochastic stream 41 of electric input pulses may originate from a sensing element of a single-photon detector which is typically a photomultiplying tube (PMT) or an avalanche photo diode (APD).

The input pulses are not required to be of the same shape. With an APD, a special avalanche quenching circuit is used, either passive or active. Typically, the APD is pre-biased into its avalanche regime, for the first photon to initiate the avalanche. To prepare for the next photon arrival, the avalanche has to be quenched. It may be advantageous to use a so-called forced-quenching circuit which regularly quenches the avalanche condition, irrespective of whether an avalanche had actually been initiated, so that the arrival of photons and the time of quenching are not correlated. As a result, the avalanche-pulse duration will be stochastic also, depending on the time of photon arrival relative to subsequent quenching.

The stream of pulses 41 is directed to an n-state cyclic state-shift device or register 42. Such a device has n successive stable states which may be numbered 0, 1, 2, . . . , n−1, with a change from a state k to its successor state k+1 being triggered by an input pulse, and with state n-1 having state 0 as its successor state. Between input pulses, the n-state cyclic state-shift device 42 retains its state. For example, for a 2-state cyclic state-shift device a flip-flop can be used, having a sequence of stable states 0, 1, 0, 1, . . . , with each input pulse causing a transition from 0 to 1 or from 1 to 0. It is not necessary that the cyclic state-shift device return to its initial state when its state is read. This is in contrast to conventional photon counters where each reading of the counter data is accompanied by resetting the state of the counter back to the initial state.

For the sake of specificity, without limiting the invention, a flip-flop will be assumed in the following further description of FIG. 4. The output from the flip-flop represents a stochastic sequence 43 of rectangular pulses of variable length. The sequence 43 is directed to a recording device 44, which can be realized as an analog or digital signal recorder. The output signal 47 is transferred from the recording device 44 to a signal processor (not shown).

The recorder of FIG. 4 operates essentially in an asynchronous mode. But, in contrast to asynchronous photon counters which record the total number of photons arriving in a particular time interval, the preferred recorder records their times of arrival. Accuracy of recording of the arrival time is controlled by the clock 45.

Time intervals are recorded without measuring the duration of the intervals. This function can be performed by one of a number of devices known to those skilled in the art, placed in an electrical circuit serially with the recorder and using its output signal 47. For example, a general-purpose computer can be used to process the array of data acquired by the recording device 44.

In some applications it may be advantageous to integrate in a single device the functions of registering the time intervals between successive single photon detections and measurement of the time intervals. Such an integrated preferred fifth embodiment of the invention is illustrated by FIG. 5, for a stochastic stream of electric pulses 51 to which the shape and APD-quenching considerations concerning pulses 41 of FIG. 4 are applicable also.

Figure 5:
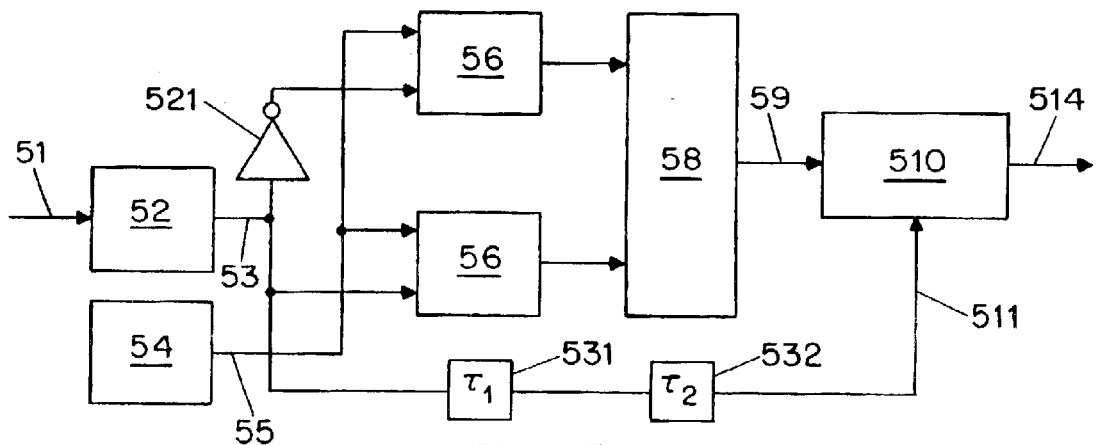
FIG. 5 is a schematic of a preferred fifth technique in accordance with the invention, wherein the fourth technique is integrated with the measurement of time intervals.

As shown in FIG. 5, a stochastic stream of electric pulses 51 is directed onto a flip-flop 52. Its output represents a stochastic sequence 53 of rectangular input pulses of variable length. The sequence 53 is split three ways between counters 56 and 56' and the controlled delay line 531. The counter 56 receives the signal from the flip-flop directly, and the counter 56' receives its signal through an inverter 521. Thus, the counters 56 and 56' are controlled by opposite-phase signals. Instead of a flip-flop, 52, an n-state cyclic state-shift device can be used, as described with reference to FIG. 4. Advantageously in this case, instead of two counters, 56 and 56', up to n counters can be used.

A clock 54 provides a regular sequence 55 of electric pulses of constant shape which are counted by the counter 56. Exemplarily, counter 56 is that counter whose input signal equals 1 at the time of clock pulse arrival. Advantageously, if the pulses 51 originate from and APD, the external quenching circuit which periodically forces the APD out of its avalanche regime can be synchronized by the clock 54. There is no advantage in increasing the quenching frequency beyond the clock frequency which provides the basic discretization of time in the technique.

When a photon is detected and an electric pulse 51 enters the flip-flop 52, one of the counters 56 and 56' stops counting and the other begins counting. The one counter that has just stopped counting then contains the record 57 of how long the interval between two successive pulses has lasted, measured in terms of the number of clock cycles counted. The record 57 is transferred to the recording device 510 through a commutator 58 which serves to provide successive recording at intervals of time so that, while one time interval is being recorded, the next one is being measured. The commutator 58 is controlled by a switch signal which is derived by input signals 53 delayed by a characteristic time $\tau_1$ corresponding to the response time of the counter 56. The output of the commutator 58 represents a sequence of codes 59 describing the measured time intervals between detected photons. The codes 59 appear at the output of the commutator 58 in stochastic fashion corresponding to the detection of incoming photons and delayed by the time interval which is the sum of $\tau_1$ and the response time $\tau_2$ of the commutator itself. It is advantageous, therefore, to control the recording device 510 by switch signals which are derived from the input signals 53, delayed from the moment of flip-flop switching by the time $\tau_1+\tau_2$. The output 514 of the recording device 510 represents the same sequence 59 of codes describing the measured time intervals between detected photons. In contrast to the sequence 59, which is accumulated in time stochastically, the sequence 514 can be transmitted in a regular fashion, e.g. at a constant rate, for further processing.

Figure 6:
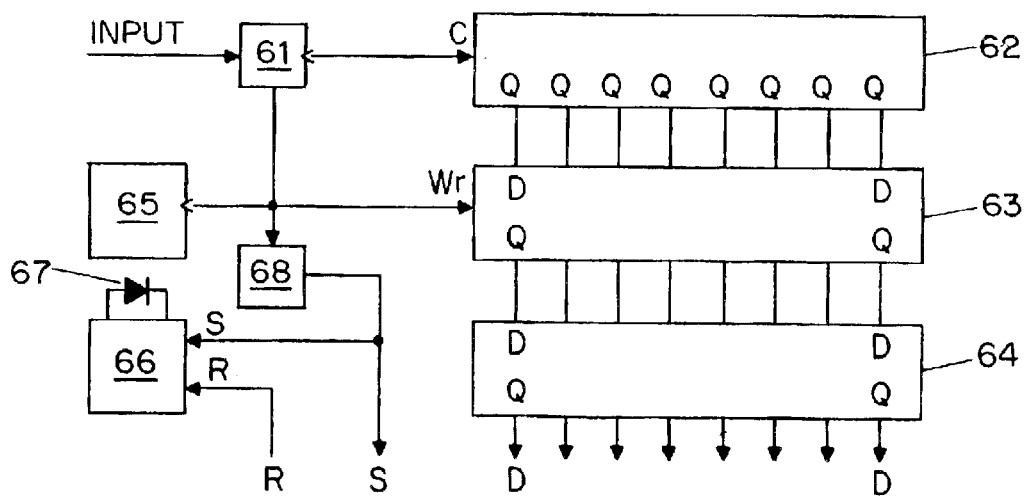
FIG. 6 is a schematic of a preferred sixth technique in accordance with the invention, wherein the fourth technique is augmented for further minimization of pulses lost to registration.

Further to the technique illustrated by FIG. 4, FIG. 6 illustrates inclusion of D-triggers for minimizing the number of pulses uncounted due their close spacing in time. Electric pulses from a single-photon detector output are directed through a fast switch 61 to the input C of a synchronous 8-bit binary counter 62. The result of the count is passed to the storage register 63 as an 8-bit word or byte. To avoid changing the state of the counter 62 during storage, the synchronous pulse generator 65 shuts off the switch 61 simultaneously with sending a short record pulse to the input Wr of the storage register 63. The output from the storage register 63 goes through the buffer 64 directly to the parallel port of a computer. Operational control error indicator is facilitate by a logic comparator 66 equipped with an LED (light emitting diode) 67. The parallel computer port is synchronized by a synchronous pulse through a delay line 68 with a suitable delay $\tau$. The same delayed pulse synchronizes the logic comparator 66.

For an exemplary embodiment of the the technique illustrated by FIG. 6, the following may be specified and realized: a discretization frequency of 125 KHz, a maximum number of pulses per discretization interval of 256, a minimum time between registered pulses of 20 ns, a maximum average frequency of registered pulses of 32 MHz, and a maximum fraction of missed photons of 0.25%.

Techniques of the invention can be used to advantage in a variety of applications involving encoded electromagnetic radiation, including multicolor luminescent detection based on fluorescence spectroscopy and fluorescence excitation spectroscopy. They can be used in general sensor applications with other modulated luminescence signals, e.g., those based on various spectroscopic techniques such as transmission, absorption, reflection, or Raman spectra, as well as electro-luminescence, chemiluminescence and the like. The techniques are especially useful for detecting weak signals, e.g. those prevalent in optical communication links where signals are transmitted over long optical fibers.

What is claimed is:

1. A method for detecting a radiated signal from an optical communication link, comprising the steps of:
    (a) detecting successive photons of an intensity-modulated signal from said optical communication link with the modulation being over time in accordance with a preselected code;
    (b) determining time intervals, each time interval being a period of time between instances of detection of two single successive photons;
    (c) recording a sequence of said time intervals; and
    (d) comparing the recorded sequence with said code.

2. Apparatus for detecting a radiated signal from an optical communication link, comprising:
    (a) a detector moiety for detecting successive photons from an intensity-modulated signal from said optical communication link, with the modulation being over time in accordance with a preselected code;
    (b) a time-interval determination moiety operationally coupled to said detector moiety for determining time intervals, each time interval being a period of time between instances of detection of two single successive photons;
    (c) a recorder moiety operationally coupled to said time-interval determination moiety for recording a sequence of said time intervals; and
    (d) a comparator moiety operationally coupled to said recorder moiety for comparing the recorded sequence with said code.

3. Apparatus for detecting a radiated signal from an optical communication link, comprising:
    (a) detector means for detecting successive photons of an intensity-modulated signal from said optical communication link, with the modulation being over time in accordance with a preselected code;
    (b) time-interval determination means operationally coupled to said detector means for determining time intervals, each time interval being a period of time between instances of detection of two single successive photons;
    (c) recorder means operationally coupled to said time-interval determination means for recording a sequence of said time intervals; and
    (d) comparator means operationally coupled to said recorder means for comparing the recorded sequence with said code.

* * * * *